(12) United States Patent
Tom et al.

(10) Patent No.: US 6,190,385 B1
(45) Date of Patent: *Feb. 20, 2001

(54) CABLE FOR BIPOLAR ELECTRO-SURGICAL INSTRUMENT

(75) Inventors: Curtis Peter Tom, West Chester, PA (US); Donald W. Regula, Belle Mead, NJ (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/210,219

(22) Filed: Dec. 11, 1998

(51) Int. Cl.[7] .................................................. A61B 18/18
(52) U.S. Cl. .............................. 606/48; 606/51; 606/34; 439/502
(58) Field of Search ................................. 606/32–40, 41, 606/45, 48, 50–52; 439/502–506, 623, 843; 174/153 G, 152 G, 151, 65 G, 135, 142, 149 R, 145

(56) References Cited

U.S. PATENT DOCUMENTS

| | | | |
|---|---|---|---|
| 4,332,434 | * 6/1982 | Neidecker et al. | 339/258 R |
| 5,026,371 | 6/1991 | Rydell et al. . | |
| 5,693,045 | * 12/1997 | Eggers | 606/50 |
| 5,776,128 | * 7/1998 | Eggers | 606/48 |
| 5,891,142 | * 4/1999 | Eggers et al. | 606/51 |
| 5,911,719 | * 6/1999 | Eggers | 606/31 |

* cited by examiner

Primary Examiner—Linda C. M. Dvorak
Assistant Examiner—Roy Gibson
(74) Attorney, Agent, or Firm—Emil Richard Skula

(57) ABSTRACT

An electrical connecting cable for bipolar electrosurgical scissors. The cable has a pair of insulated parallel conductors having insulating coatings. The coatings are separably connected. A slidable grommet is mounted to the cable. The conductors are partially separable from each other. A plug is mounted to one end of the cable. Spring loaded connectors are mounted to the other end of the cable.

8 Claims, 4 Drawing Sheets

CABLE FOR BIPOLAR ELECTRO-SURGICAL INSTRUMENT

TECHNICAL FIELD

The field of art to which this invention relates is bipolar electrosurgical instruments, more particularly, cables for use with bipolar electrosurgical instruments.

BACKGROUND OF THE INVENTION

Electrosurgical instruments are well known in the surgical arts. These instruments utilize radio frequency energy provided by a generator to power electrosurgical instruments having various configurations, e.g., pencils, probes, electrosurgical scissors, electrosurgical forceps, etc. The instruments, when in contact with tissue, allow for the passage of a high frequency current along a pathway from an active electrode, through tissue, and then to a ground or return electrode. The current flow allows the surgeon to cut or coagulate tissue by varying parameters such as power, contact time, wave form, frequency, etc.

There are two types of electrosurgical systems that are commonly used: monopolar systems and bipolar systems. The monopolar systems use an instrument with a single active electrode. A grounding pad having a substantially large surface area is mounted to the patient's body to provide a return path back to the generator. In a monopolar system, current will flow from the active electrode on the instrument, to the tissue site, and then through the patient's body to the grounding pad. In contrast, bipolar systems typically utilize an instrument having both an active electrode and a return electrode mounted to the instrument. A patient grounding pad with its attendant disadvantages is not required. The current path in a bipolar system is from the active electrode, through the tissue site, and then back to the return electrode. The current path is much more localized in a bipolar system when compared to a monopolar system.

An electrosurgical system will typically consist of an electrosurgical generator, an electrosurgical probe or instrument, and a connecting cable. Conventional electrosurgical cables must provide conductors having sufficient size to safely conduct the electrosurgical power produced by the generator. The cables must be flexible and compact and must have sufficient electrical insulation. The cables must have connectors on both ends for electrically connecting the generator to the instrument. Since there is a fundamental difference in the operation of bipolar and monopolar electrosurgical instruments, it is an important safety consideration to prevent bipolar instruments from being inadvertently connected to monopolar electrosurgical generators. In addition, bipolar instruments typically have two electrical connectors while monopolar instruments only require one connector, i.e., the grounding pad is connected separately to the generator. Bipolar instruments must be designed so that the additional electrical connector and cable does not impede the surgeon when using the bipolar instrument in a surgical procedure.

Cables know in this art may be made from conventional co-axial cable or conventional "zip" cable. The cables typically have banana plug connectors mounted on one or both ends. One end of a cable is connected to an electrosurgical generator, while the other end of the cable is connected to an electrosurgical instrument. The cables may also have specially configured plugs on the generator end so that the cable can be used with only specific types of generators, for example, for use only with bipolar generators.

Although conventional bipolar cables perform adequately, there are several problems attendant with their use, including adjustability of cable length and secure mounting to terminal posts. In addition, when using a bipolar instrument such as bipolar scissors which have electrodes that are moveable with respect to each other, conventional bipolar cables may be deficient since they do not allow for such movement.

Accordingly, there is a need in this art for improved bipolar cables, and for bipolar cables that can be used with bipolar instruments having moveable electrodes such as bipolar electrosurgical scissors.

SUMMARY OF THE INVENTION

Therefore, it is an object of the present invention to provide a bipolar cable for bipolar electrosurgical instruments having a pair of conductors that are separable along the length of the cable, and wherein the length of the separated section is adjustable.

It is a further object of the present invention to provide a bipolar cable having connectors that adjust to securely mount to variously sized connector terminal posts.

It is yet a further object of the present invention to provide a novel cable for use with bipolar instruments that have moveable electrodes, such as bipolar electrosurgical scissors.

Accordingly, a bipolar cable for bipolar electrosurgical instruments is disclosed. The cable has a distal end and a proximal end and a length. The bipolar cable has a pair of parallel insulated electrical conductors consisting of electrically conductive wires having electrically insulating coatings. Each conductor has a distal end and a proximal end. The conductors are mounted parallel to each other by connecting the insulative coatings to each other along the length of the conductors. The conductors may be separated from each other along a section of the length by pulling the distal ends of the conductors apart thereby separating the insulating coatings apart. A slidable grommet member is mounted over the conductors. A spring loaded connector is mounted to the distal ends of each conductor in electrical contact with the wires. Optionally, a bipolar generator plug is mounted to the proximal ends of the conductors for engagement with a bipolar electrosurgical generator. The length of the separation of the conductors from each other may be changed by sliding the grommet along the conductors, thereby maintaining separated segments of the conductors together.

Yet another aspect of the present invention is the above described bipolar cable in combination with a bipolar electrosurgical instrument such as a bipolar scissors instrument having electrodes that are moveable with respect to each other.

Still yet another aspect of the present invention is a method of using the cable of the present invention with a bipolar surgical instrument having electrodes that are moveable with respect to each other.

These and other aspects and advantages of the present invention will become more apparent from the accompanying drawings and detailed description.

DESCRIPTION OF PREFERRED EMBODIMENTS

Figure 1:
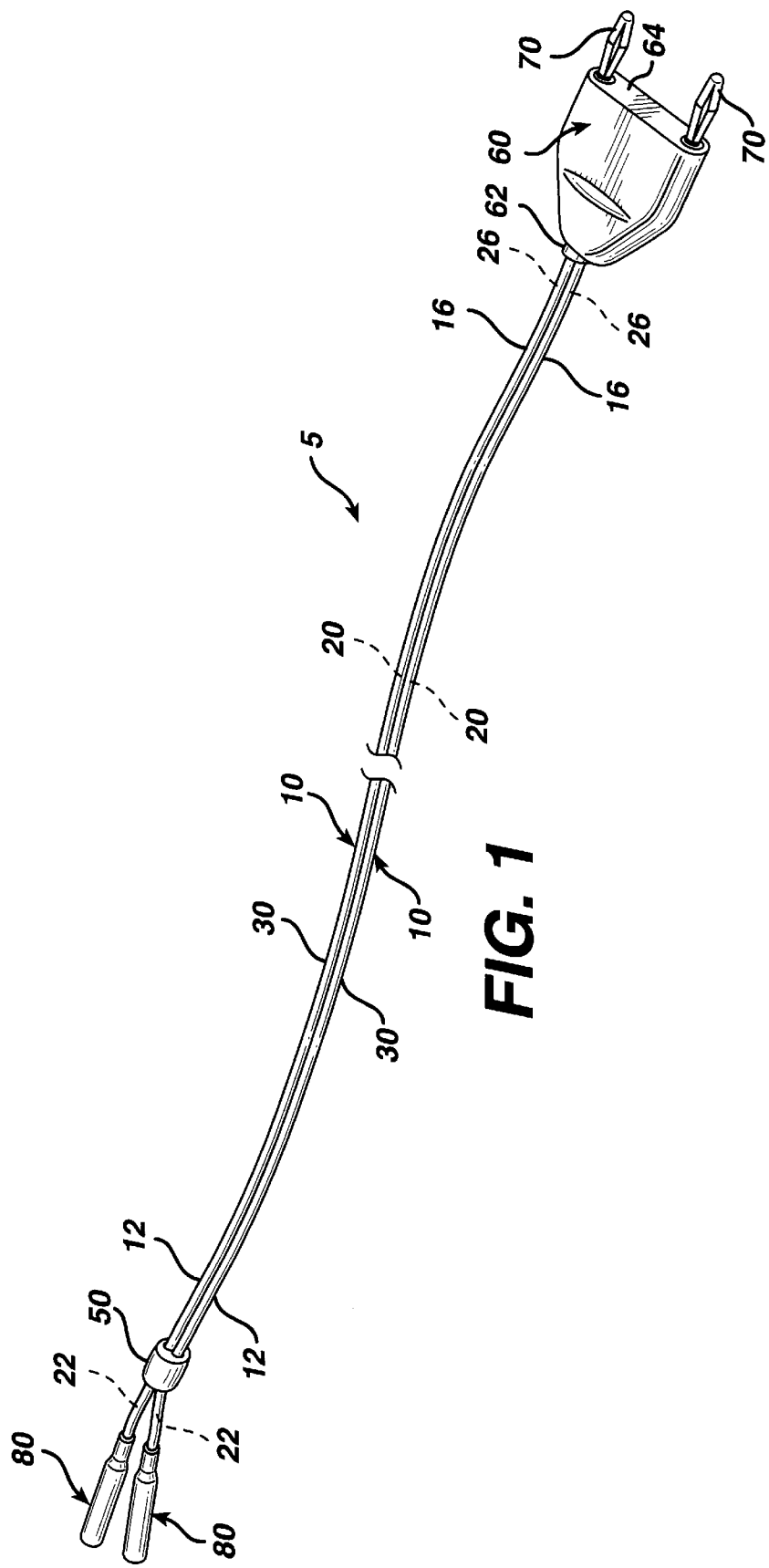
FIG. 1 is a perspective view of the bipolar cable of the present invention.
Figure 2:
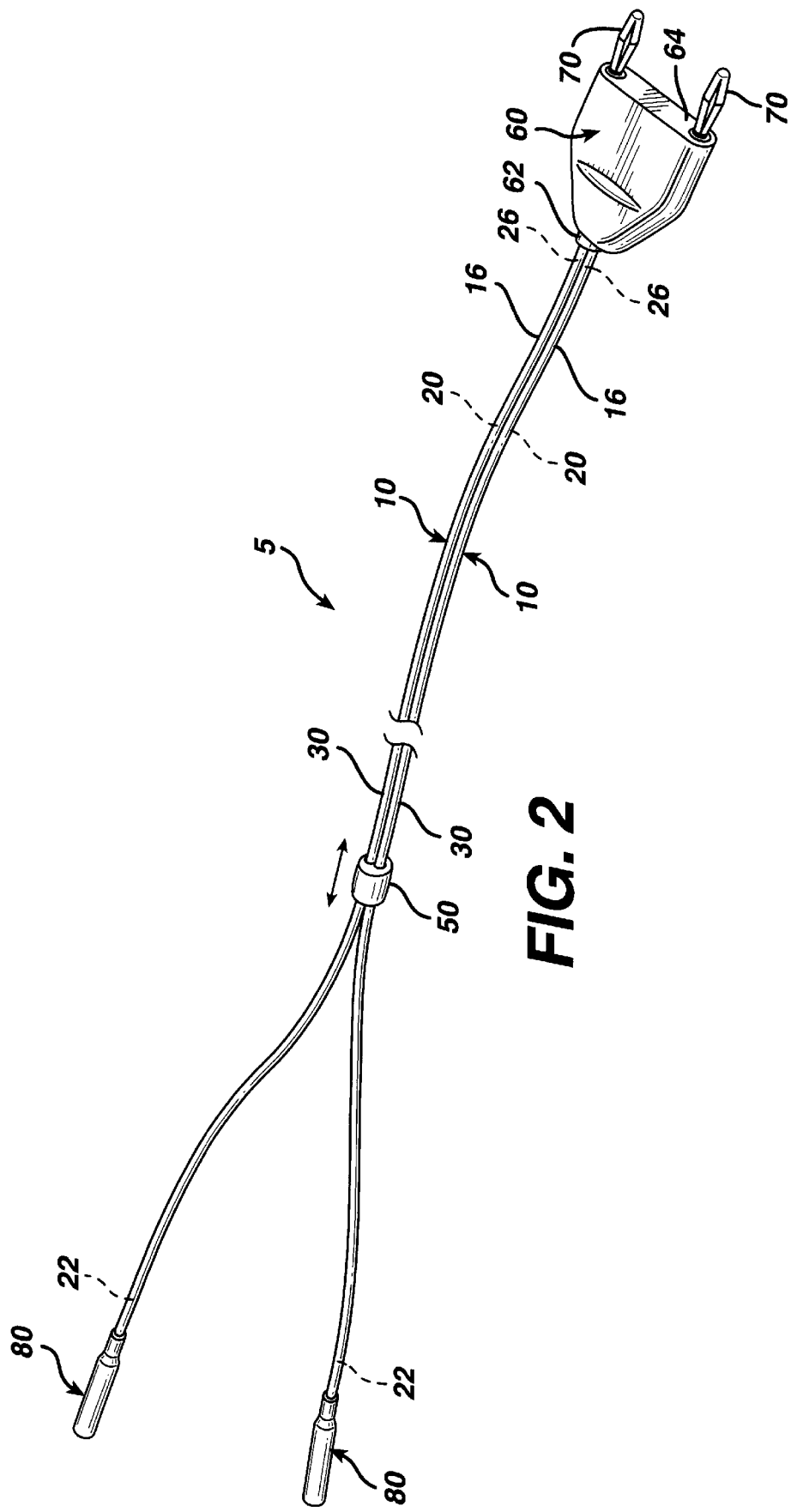
FIG. 2 is a partial perspective view of the cable of FIG. 1 illustrating the adjustability of the length of the conductor separation by sliding a grommet along the conductors, after a segment of the cable has been separated by pulling apart.
Figure 3:
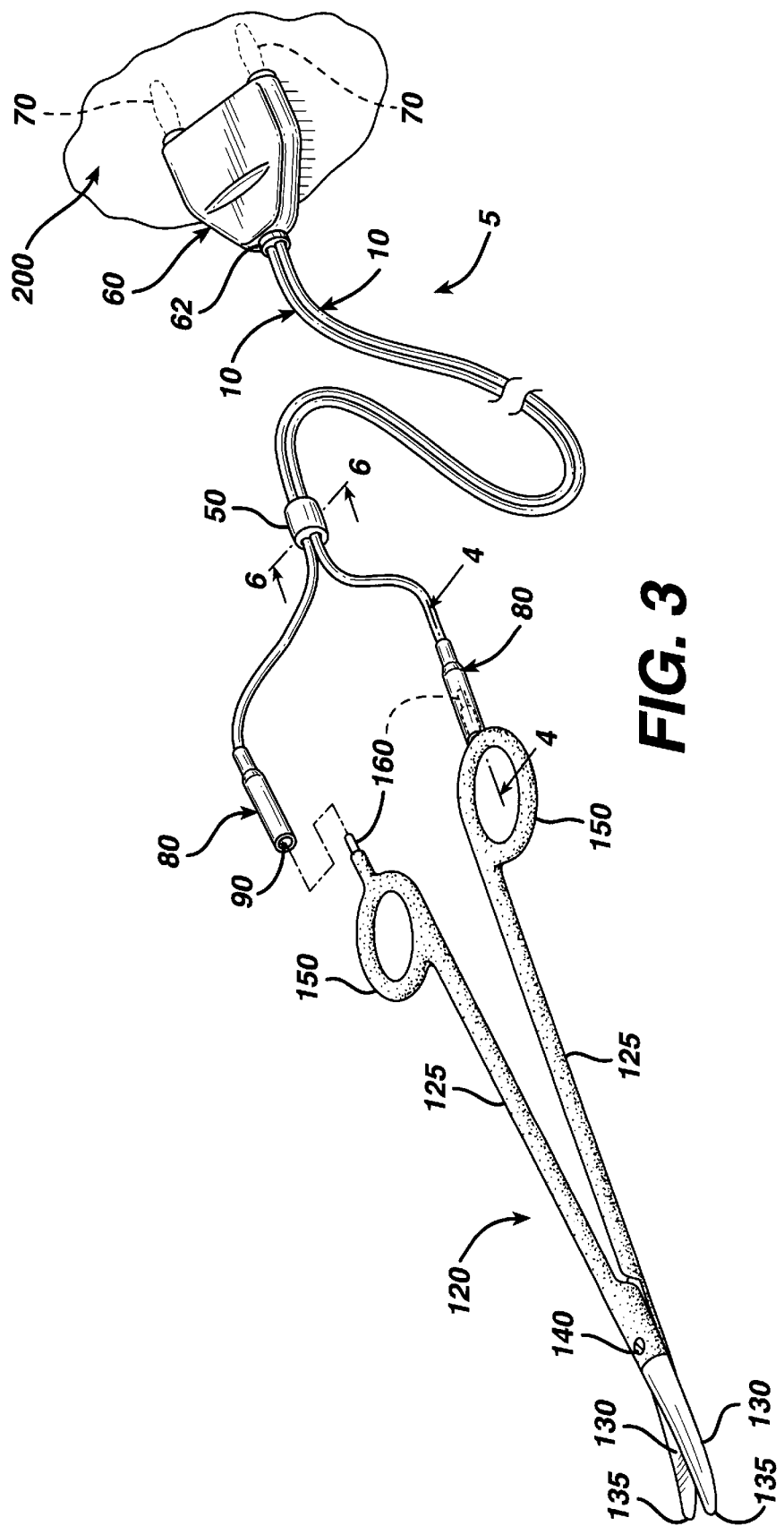
FIG. 3 is a perspective view of the cable of the present invention showing the proximal plug end mounted in an electrosurgical generator and the distal spring loaded connectors mounted to the terminals of a bipolar electrosurgical scissors instrument.
Figure 5:
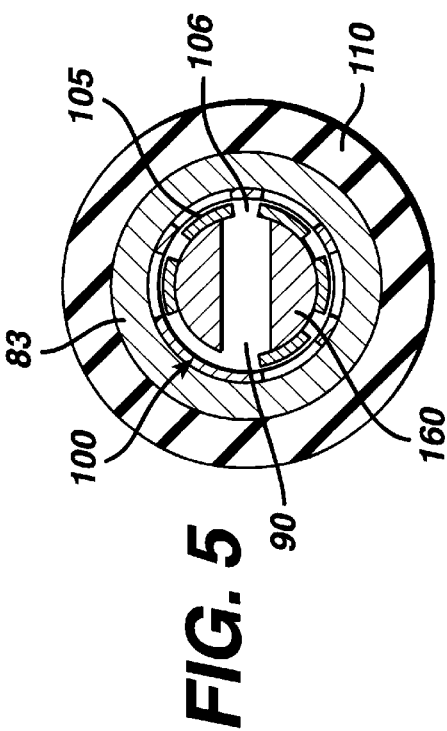
FIG. 5 is a cross-sectional view taken along view line 5—5 of FIG. 4 illustrating the spring member with the spring loaded connector.

A cable 10 of the present invention is illustrated in FIGS. 1, 2, and 3. As seen in FIG. 1, the cable 5 has a pair of parallel elongated electrical conductors 10. The conductors 10 have distal ends 12 and proximal ends 16. Conductors 10 are also seen to have interior electrically conductive wire members 20 having distal ends 22 and proximal ends 26. Wires 20 may be conventional single strand or multistrand wires or coaxial wires or cables. Referring also to FIG. 5, it is seen that the conductors 20 have electrically insulative coating 30 along their entire length. Insulative coatings 30 are made from conventional electrically insulative polymeric materials, mineral materials and the like and combinations and equivalents thereof. The insulative coatings 30 for each conductor are seen to be connected to each other at connection 35 along at least part of their length. The connection 35 is preferably designed so that the coatings 30 of conductors 10 are separable from each other along connection 35 by pulling the distal ends 12 of conductors 10 apart. Preferably, connection 35 is formed by co-extruding the coatings 30 onto wires 20. Alternatively, the insulative coatings can be mounted or connected to each other at connecting point 35 through conventional means such as melt fusing, adhesives, ultrasonic or heat welding, and the like. The coatings 30, however, should be separable from each other by minimal exertion of force on distal ends 12, while not separating from the wires 20.

Mounted to conductors 30 in a slidable fashion is the grommet member 50. Grommet member 50 is seen to be a substantially cylindrically shaped member having a central passage therethrough, although grommet 50 may have any shape including oval, rectangular, polygonal, square, and the like and combinations thereof. The central passage is seen to have a configuration that has a cross-section substantially similar to the cross section of the cable 5 and conductors 10. Preferably, the passage way 55 will be dimensioned such that there is a slight resistance to movement or sliding over the conductors 10 such that the grommet 50, when moved to a position along the length of cable 10 and conductors 10, will remain in a fixed position. Grommet 50 is preferably made from the same types of electrically insulative materials used for the coatings 30. Mounted to the proximal end 16 of the conductors 10 is the generator plug member 60. Generator plug member 60 is seen to have distal end 60 for receiving the proximal end 16 of conductors 10 and proximal face 64. Extending proximally from proximal face 64 of the plug member 60 are the mounting plugs 70. Mounting plugs 70 are seen to be elongated conventional electrically conductive plug members that are electrically connected to wires 20. As seen in FIG. 3, the plugs 70 are inserted into receptacles in a conventional bipolar electrosurgical generator 200 (partially shown). Plug member 60 is designed to prevent the plug from being inserted into a conventional monopolar generator. If desired, plug member 60 may be replaced by conventional flying banana plugs mounted to the proximal ends 16 of cable conductors 10.

Figure 4:
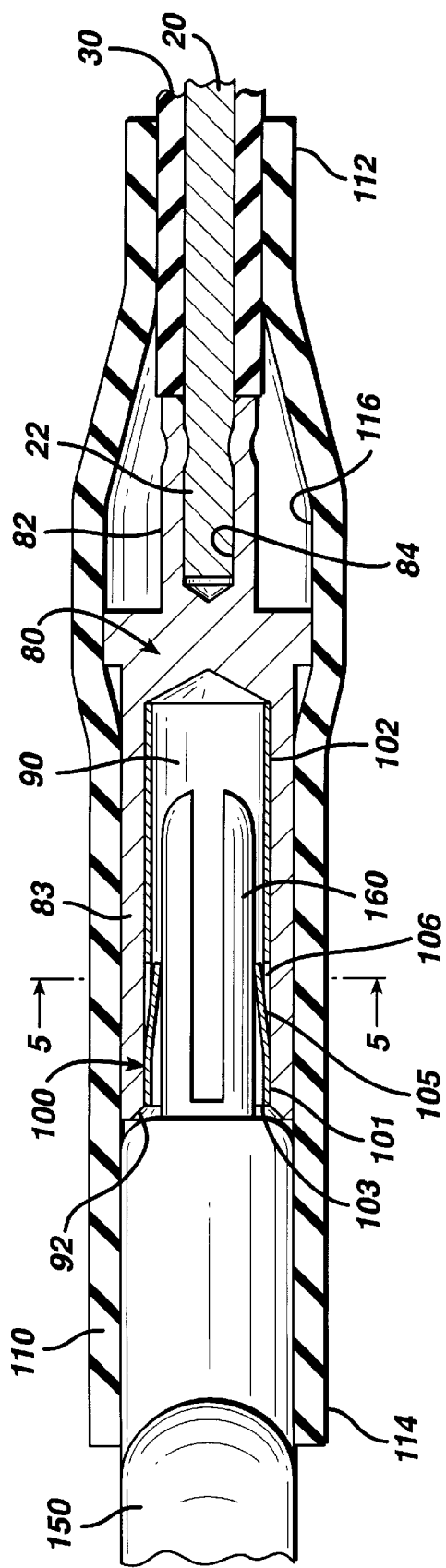
FIG. 4 is a partial cross-sectional view taken along View Line 4—4 of FIG. 3, illustrating a spring loaded connector mounted to a terminal of the bipolar scissors.
Figure 6:
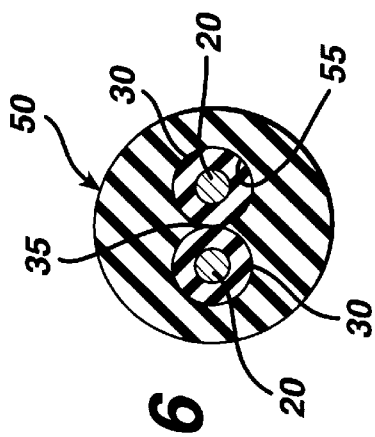
FIG. 6 is a cross-sectional view taken along View Line 6—6 of FIG. 3 showing the insulated conductors within the grommet.

Mounted to the distal ends 22 of the conductors 20, as seen in FIGS. 1, 4, and 5 are the spring-loaded connector members 80. Members 80 are made from an electrically conductive material, preferably metal. Spring-loaded connector members 80 are seen to have proximal end 82 having cavity 84 for receiving end 22 of wire 20. Connector member 80 is also seen to have a distal cavity 90 adjacent to proximal end 83 having opening 92. Distal spring member 100 having prongs 105 separated by slots 106 is seen to be mounted in passage 90. Spring member 100 is substantially cylindrical in shape tapering inward along its length from distal end 101 to proximal end 102. The member 100 also has distal opening 103. In a resting configuration, the prongs 105 are situated relatively close to each other and are separated by slots 106. The prongs are moved apart from each other are upon the insertion of mounting post 160 into cavity 90 and exert a spring force upon the outer surface of post 160, thereby maintaining it within cavity 90. The spring member 100 is preferably made from an electrically conductive spring metal such that when the prongs 105 are separated they exert a biasing force upon the prong 160. The spring member 100 is mounted in cavity 90 by a force fit or other conventional of mounting manner (e.g., soldering, brazing, etc.) such that the spring member 100 is in electrical contact with the member 80. The spring loaded conductor 80 is seen to be covered by tubular member 110 having proximal end 112, distal end 114 and internal passage 116. Member 110 extends proximally past proximal end 82 onto conductor 10, and extends distally beyond the distal end 83 of member 80.

Tubular member 110 is preferably made from a flexible, expandable electrically insulating polymeric material. Wires 20 are made from conventional electrically conductive materials including copper, silver, aluminum and equivalents thereof. Insulative coating 130 may be made from conventional polymeric or mineral, electrically insulative materials and equivalents and combinations thereof.

A bipolar scissors instrument usable with cables 5 of the present invention is seen in FIG. 3. The scissors 120 is seen to have blade members 125. The blade members 125 are seen to have proximal finger grips 150 and distal tips 135. Extending from the distal end of the blade members 125 are the cutting blades 130. Blade members 125 are connected by insulated pivot screw member 140 such that the blade members 125 can pivot about the pivot screw member 140 with respect to each other. Blade members 125 are seen to have an insulative coating running from the finger grips 150 to just distal of the insulated screw 140. Extending proximally from each finger grip 150 are the electrically conductive electrode posts 160. Electrode posts 160 are insertable into cavities 90 of spring-loaded connectors 80. The electrode posts 160 are movable with respect to each other when the scissors are used and the blade members 125 rotate about pivot screw 140. This movement is permitted by the novel cable 5 of the present invention.

Referring to FIGS. 2 and 3, it will be appreciated by those skilled in the art that the degree of separation of the conductors 20 will depend on the characteristics of the instrument such as a scissors, as well as the characteristics of the hand of the user. The use of the cables 5 of the present invention allows the user to adjust the cable 5 to compensate for variations in scissor cutting stroke or electrode movement of the instrument, as well as the size of the hand of the surgeon. In addition, the spring-loaded connectors 80 compensate for wear or damage to the posts 160 and maintain the posts 160 both mechanically in cavity 90 and in electrical contact with members 80 when the posts move with respect to each other during a surgical procedure. It can be appreciated by those skilled in the art that electrode posts may vary in size from instrument to instrument, and that post dimensions of any given instrument may vary over time due to wearing or damage. In addition, the magnitude of the relative movement of electrodes on the instrument will vary from instrument to instrument. Furthermore, the cables 10 are useful for bipolar electrosurgical instruments that have moveable electrodes.

The connecting cables of the present invention allow for the connection to an electrosurgical generator of electrosurgical instruments having movable electrodes. The surgeon is able to compensate for differences in movement depending on the type of instrument utilized, for example, difference scissor types, and also compensate for individual differences in scissor stroke and user hand size. In addition, the surgeon is assured that the cable will maintain electrical contact with the scissors electrode posts due to the spring loaded connectors mounted to the conductors.

Although this invention has been shown and described with respect to detailed embodiments thereof, it will be appreciated by those skilled in the art that various changes in form and detail thereof may be made without departing from the spirit and scope of the claimed invention.

We claim:

1. A bipolar cable for a bipolar surgical instrument, comprising:
    a pair of parallel conductors, the conductors comprising an electrically conductive wire having an electrically insulating coating, each conductor having a length, a distal end and a proximal end, wherein the insulating coatings are separably connected to each other along substantially the entire lengths of the conductors wherein said conductors may be separated from each other along a length by pulling the distal ends of the conductors apart;
    a grommet member slidably mounted on the conductors, said grommet member having an interior passage for receiving the conductors;
    a spring-loaded electrical connector mounted to the distal end of each conductor;
    a tubular electrically insulated member mounted over the spring-loaded connector; and,
    a bipolar generator plug mounted to the proximal ends of the conductors for engagement with a bipolar electrosurgical generator said plug having a pair of electrically conductive mounting posts,
    wherein the length of the separation of the conductors may be changed by sliding the grommet along the conductors.

2. The cable of claim 1 wherein the cable is used with a bipolar surgical instrument having electrodes which are moveable with respect to each other.

3. The cable of claim 1 wherein the spring loaded connector comprises:
    an elongated cylindrical frame having a proximal cavity for receiving a wire and a distal cavity for receiving an electrode post; and,
    a tubular spring member mounted in the distal cavity for engaging the post.

4. The combination comprising:
    A) a bipolar cable for a bipolar instrument comprising:
        a pair of parallel conductors, the conductors comprising electrically conductive wire having an electrically insulating coating, each conductor having a length a distal end and a proximal end, wherein the insulating coatings are separably connected to each other along substantially the entire lengths of the conductors, wherein said conductors may be separated from each other along a length by pulling the distal ends of the conductors apart;
        a grommet member slidably mounted on the conductors, said grommet member having an interior passage for receiving the conductors;
        a spring loaded electrical connector mounted to the distal end of each conductor;
        a tubular electrically insulated member mounted over the spring-loaded connector; and,
        a bipolar generator plug mounted to the proximal ends of the conductors for engagement with a bipolar electrosurgical generator said plug having a pair of electrically conductive mounting posts,
        wherein the length of the separation of the conductors may be changed by sliding the grommet along the conductors; and,
    B) a bipolar surgical instrument having two electrically conductive posts, wherein the instrument has electrodes that are moveable with respect to each other and wherein the spring loaded connectors are mounted to the conductive posts.

5. The combination of claim 4 wherein the spring loaded connector comprises:
    an elongated cylindrical frame having a proximal cavity for receiving a wire and a distal cavity for receiving an electrode post; and,
    a tubular spring member mounted in the distal cavity for engaging the post.

6. The combination of claim 4 wherein the instrument comprises a bipolar electrosurgical scissors.

7. A method of using a bipolar electrosurgical device, the method comprising:
    providing a bipolar surgical instrument comprising two electrically conductive posts wherein the instrument has electrodes that are moveable with respect to each other;
    providing a cable comprising:
        a pair of parallel conductors, the conductors comprising electrically conductive wire having an electrically insulating coating, each conductor having a length a distal end and a proximal end, wherein the insulating coatings are separably connected to each other along substantially the entire lengths of the conductors, wherein said conductors may be separated from each other along a length by pulling the distal ends of the conductors apart;
        a grommet member slidably mounted on the conductors, said grommet member having an interior passage for receiving the conductors;
        a spring loaded electrical connector mounted to the distal end of each conductor;
        a tubular electrically insulated member mounted over the spring-loaded connector; and,
        a bipolar generator plug mounted to the proximal ends of the conductors for engagement with a bipolar electrosurgical generator said plug having a pair of electrically conductive mounting posts, wherein the length of the separation of the conductors may be changed by sliding the grommet along the conductors;

separating the cable along a section of its length by pulling the distal ends of the cable apart;

moving the grommet adjacent to the section of cable that has been separated;

mounting the plug in an electrosurgical generator;

mounting the spring loaded connectors to the electrode posts; and, actuating the instrument.

8. The method of claim 6, wherein the instrument comprises bipolar electrosurgical scissors.

* * * * *